United States Patent [19]

Gobby

[11] Patent Number: 4,474,576
[45] Date of Patent: Oct. 2, 1984

[54] APPARATUS FOR ARTIFICIAL INSEMINATION

[76] Inventor: Kevin W. Gobby, 14 Rickman St., Balcatta, Western Australia, Australia

[21] Appl. No.: 403,659

[22] PCT Filed: Dec. 3, 1981

[86] PCT No.: PCT/AU81/00178
§ 371 Date: Aug. 2, 1982
§ 102(e) Date: Aug. 2, 1982

[87] PCT Pub. No.: WO82/01825
PCT Pub. Date: Jun. 10, 1982

[30] Foreign Application Priority Data
Dec. 3, 1980 [AU] Australia .............................. PE6743

[51] Int. Cl.³ ........................ A61D 7/02; A61M 37/02
[52] U.S. Cl. ..................................... 604/176; 604/115; 604/181; 604/218; 604/264; 128/343
[58] Field of Search ................. 604/55, 115, 176, 181, 604/218, 212, 264, 275-278, 40-42; 128/343, 3-8, 17

[56] References Cited
U.S. PATENT DOCUMENTS

| 699,594 | 5/1902 | Van Schott | 604/218 X |
| 1,422,490 | 7/1922 | Stader | 604/218 |
| 2,587,984 | 3/1952 | Edwards | 604/218 X |
| 2,855,932 | 10/1958 | Stubbs | 604/176 X |
| 3,096,764 | 7/1963 | Uddenberg | 604/176 |
| 3,380,453 | 4/1968 | Leveille | 604/217 |
| 3,685,509 | 8/1972 | Bentall | 604/115 X |
| 4,173,227 | 11/1979 | Cassou et al. | 604/218 |

FOREIGN PATENT DOCUMENTS

| 2432866 | 4/1980 | France | 604/55 |
| 2450102 | 10/1980 | France | 604/55 |

Primary Examiner—Dalton L. Truluck
Attorney, Agent, or Firm—Harness, Dickey & Pierce

[57] ABSTRACT

The invention relates to apparatus for artificially inseminating humans and other animals of the type having a reproductive system which includes a vagina and a uterus. The apparatus consists of a locating tube which is adapted to be inserted into the vagina of the human or animal and one end of the tube located against the cervix of the uterus around the cervical canal. A delivery member is adapted to be passed along the locating tube and into the uterus for delivery of semen into the uterus.

17 Claims, 6 Drawing Figures

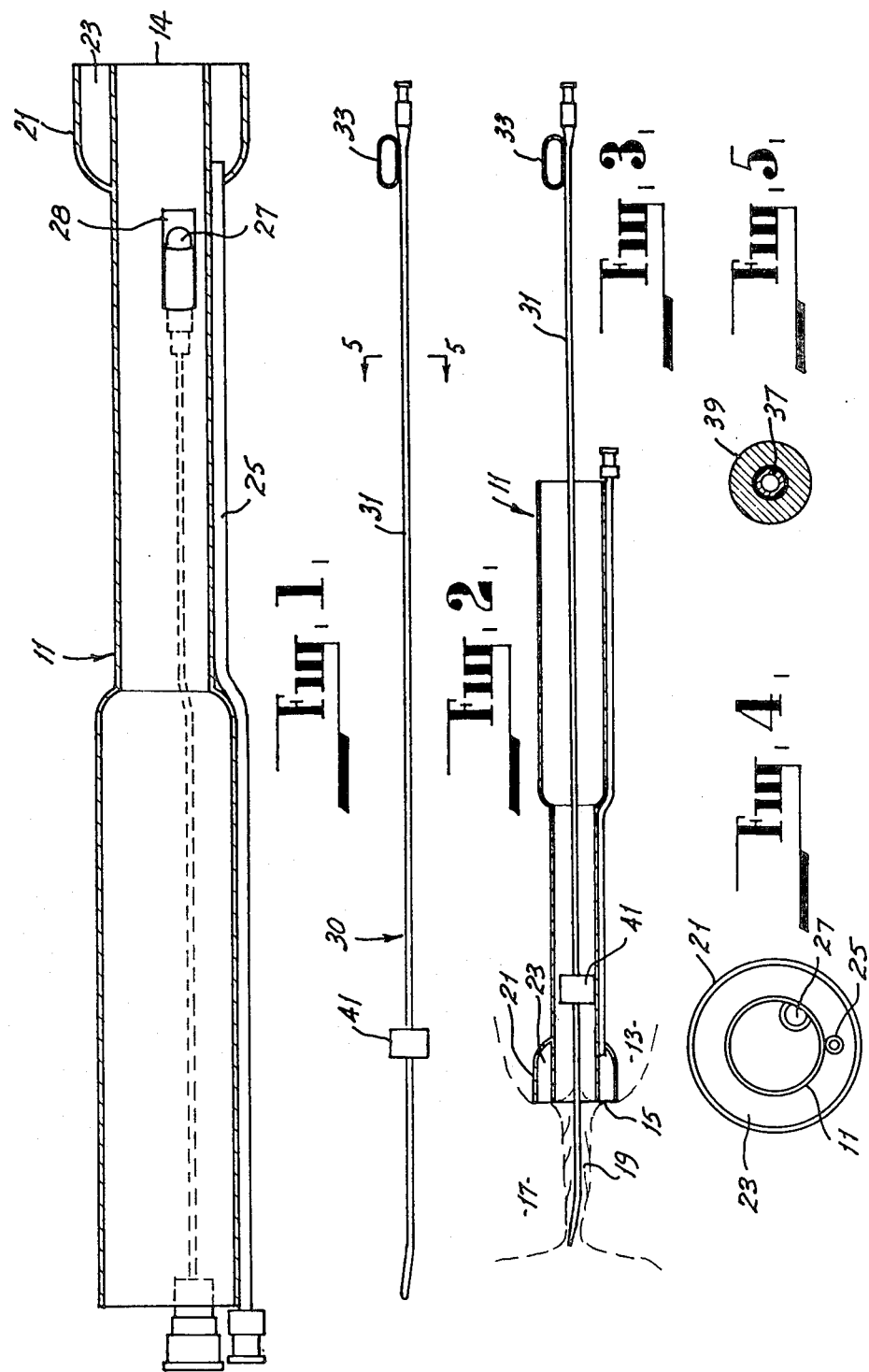

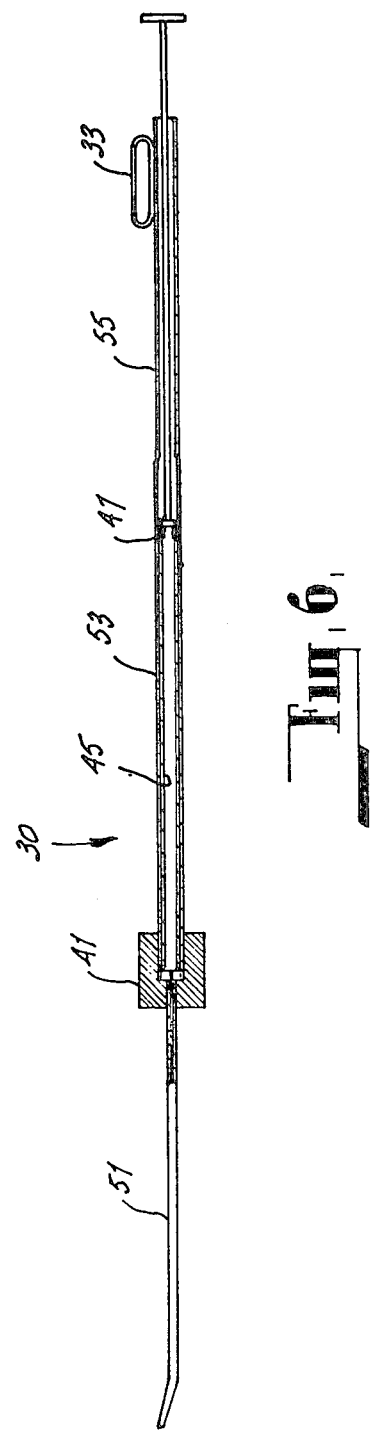

APPARATUS FOR ARTIFICIAL INSEMINATION

This invention relates to an apparatus for artificial insemination of humans and other animals of the type having a reproductive system which includes a vagina and a uterus.

Artificial insemination of humans and other animals of the type having a reproductive system which includes a vagina and a uterus involves the delivery of a charge of semen to the uterus. One technique of artificial insemination involves locating the cervical canal of the animal with the aid of a speculum and then inserting a catheter along the vagina and cervical canal and into the uterus for delivery of semen loaded in the catheter to the uterus. However, the anatomy of sheep is such that it is almost impossible to pass the catheter along the cervical canal using this technique, and it is therefor necessary to deposit the semen in the cervical canal rather than in the uterine cavity. The spermatozoa carried by the semen is therefore required to pass along the cervical canal and into the uterus before conception can take place. As a result of this, the success rate of the insemination technique is not as high as it would be if the semen could be deposited in the uterine cavity.

It is an object of this invention to provide apparatus for artificial insemination of humans and other animals of the type having a reproductive system which includes a vagina and a uterus, which apparatus enables a charge of semen to be deposited in the uterine cavity of the human or animal.

In one form the invention resides in apparatus for artificial insemination of humans and other animals of the type having a reproductive system which includes a vagina and a uterus, said apparatus comprising a locating tube adapted for insertion into the vagina whereby one end of the tube locates against a cervix of the uterus around the cervical canal, and a delivery member adapted to be passed along the locating tube and into the uterus for delivery of semen into the uterus.

According to a preferred feature of the invention, there is provided means for releasably securing said one end of the locating tube to the cervix.

The locating tube may be releasably secured at said one end to the uterus by means of a suction force applied between the locating tube and the cervix.

The invention will be better understood by reference to the following description of one specific embodiment thereof as shown in the accompanying drawings in which:

FIG. 1 is a sectional elevational view of the locating tube of apparatus according to the embodiment;

FIG. 2 is a schematic elevational view of one form of the delivery member;

FIG. 3 is a schematic view in which the locating tube is shown located against the uterus of an animal and the delivery member of FIG. 2 shown inserted through the cervical canal and into the uterine cavity (the anatomy of the animal being depicted by the phantom lines);

FIG. 4 is an elevational view of the end of the locating tube which is adapted to locate against the uterus of the animal;

FIG. 5 is an enlarged cross-section on the line 5—5 of FIG. 2;

FIG. 6 is a partly sectioned schematic elevational view of an alternative form of the delivery member.

The embodiment shown in the drawings is directed to apparatus for artificial insemination of sheep. The apparatus comprises a locating tube 11 adapted for insertion into the vagina 13 of the animal whereby one end 14 of the locating tube locates against a cervix 15 of the uterus 17 around the cervical canal 19.

A skirt 21 surrounds that portion of the locating tube adjacent said one end 14 whereby a suction chamber 23 is defined between the skirt 21 and that portion of the locating tube which the skirt surrounds. The suction chamber 23 is open at the end thereof adjacent said one end 14 of the locating tube, and said open end of the suction chamber is adapted to be closed-off by the cervix of the animal when the end 14 of the tube is located against the cervix; thus, the locating tube may be retained in engagement with the uterus under the action of a suction force when a vacuum or partial vacuum is applied to the suction chamber. In the illustrated arrangement, the skirt 21 is rigid and its side wall is spaced from the locating tube so as to define the suction chamber 23. The inner end of the skirt merges with the locating tube and the corresponding end of the suction chamber is thereby closed. The outer end of the skirt 21 is substantially flush with said one end 14 of the tube so that both the outer end of the skirt and said one end 14 of the tube may sealingly engage the cervix of the uterus and thereby seal the open end of the suction chamber 23. In an alternative arrangement, the skirt may be of flexible nature, with the outer end of the skirt extending beyond the end 14 of the locating tube, whereby the skirt deflects to conform with the cervix and sealingly engage the cervix when the end 14 of the tube is located against the cervix.

An air line 25 extends axially along the locating tube 11 on the outer side thereof and communicates at one end with the suction chamber 23. The other end of the air line is adapted for connection to a vacuum source (not shown), such as a vacuum pump, whereby vacuum or partial vacuum may be applied to the suction chamber.

A light source 27 is mounted on the locating tube adjacent said one end 14 thereof. The purpose of the light source, when in operation, is to make the cervix of the animal clearly visible to a user of the apparatus when the user peers along the locating tube from the end thereof remote from said end 14. The light source is electrically operated and is mounted in a recess formed in the outer side wall of the locating tube. Light from the light source enters the locating tube through an aperture 28 formed in the side wall of the tube.

A delivery member is adapted to be passed along the locating tube and into the uterus for delivery of a charge of semen into the uterus. The delivery member shown in FIG. 2 of the drawings comprises a delivery tube one end of which is adapted for connection to a supply of semen and the other end of which is offset so as to be inclined to the longitudinal axis of the tube, the inclination preferably being between 2° and 5°. A marker 33 is provided on the delivery tube at a location remote from said offset end to provide the user with an indication of the direction of the offset. The delivery tube itself comprises an inner tube 37 along which the semen is passed and an outer tube 39 which provides the inner tube with lateral stability (as best seen in FIG. 5). In the illustrated embodiment, the inner tube 37 has an internal diameter of 0.5 mm, and the outer tube 39 has an external diameter of 3 mm. The inner and outer tubes are connected together at the respective ends. The supply of semen may be contained in a hypodermic syringe barrel to which said one end of the delivery tube is coupled by means of a luer-lock fitting assembly or the like. It should be appreciated that any other suitable means may be provided for introducing semen into the delivery tube and causing it to pass therealong and ultimately discharge from said other end of the delivery tube.

The delivery tube 31 is provided with a protrusion 41 such as a boss, located towards the end thereof provided with the offset. The boss is preferably formed from a transparent material so that the user may see beyond the boss; in this way, the boss does not obsure the users view of the cervix when the delivery tube is positioned in the locating tube. When the delivery tube 31 is inserted into the locating tube 11, the boss 41 is able to rest on the inner side wall of the locating tube and thereby provide a fulcrum about which the delivery tube 31 may be pivoted; in this way, the end of the delivery tube 31 which is provided with the offset may be caused to undergo lateral movement on pivotal movement of the delivery tube about the fulcrum. The end portion of the locating tube 11 remote from the said one end 14 thereof is of enlarged cross-section with respect to the end portion adjacent said one end to allow for increased angular movement of the delivery tube as it is pivoted.

An alternative arrangement of delivery member 30 is illustrated in FIG. 6 of the drawings. With this arrangement, the delivery member is adapted to receive a tube 45, commonly known as a "french mini-straw" in which semen is stored (normally in a frozen condition). The straw is normally closed at one end by a removable cap and at the other end by a plug 47 which is adapted to be pushed along the tube, after the semen has thawed and said cap being removed, to cause the semen to discharge from said one end of the straw.

The delivery member comprises a delivery section 51, a storage section 53 and a plunger section 55. The delivery section 51 is of tubular form 53 is adapted for connection at one of its ends to the delivery section and at its other end to the plunger section. The storage section is tubular and is adapted to receive the straw 45, with said cap on said one end thereof removed, in a manner such that said one end is located adjacent the delivery section 51 and said other end is located adjacent the plunger section 55. The plunger section is provided with a plunger 57 one end of which is adapted to bear on the plug 47. The plunger 57 is arranged to be actuated by the user so as to cause the plug 47 to advance along the part of the length of the straw in the direction towards said one end thereof and therefore cause semen to discharge from said one end. The semen which has discharged from the straw 45 passes along the delivery section and discharges from the outlet end thereof. It is the delivery section 51 of the delivery member that is actually passed along the cervical canal and into the uterine cavity. The plunger is preferably provided with means for providing an indication of, or selectively controlling, the extent of movement of the plunger so that the user may be aware of the quantity of semen deposited by the delivery member.

As with the arrangement illustrated in FIG. 2, the delivery member is provided with a protrusion 41, such as a transparent boss. In addition, the free end portion of the delivery section is off-set.

To artificially inseminate a ewe, the ewe is presented for insemination by raising her hind-quarters and securing her hind-legs to prevent kicking. The outer tube is then inserted into the vagina of the ewe until the end 14 thereof locates against the cervix. With the light source 27 operating, the user peers along the locating tube and adjusts its position so that the end 14 of the tube is positioned the cervical canal. A vacuum or a partial vacuum is then applied to the suction chamber 23 to apply a suction force between the locating tube and cervix and thereby secure the locating tube to the uterus. The delivery member is then passed along the locating tube 11 and the offset end of the delivery member presented to the entry of the cervical canal. The user must then manipulate the delivery member to lift at least one of a series of flaps at the entry of the cervical canal so that entry to the canal may be gained; it is for this reason that the end of the delivery member is offset. The user is able to lift the flaps by pivoting the delivery member about the fulcrum formed by the boss, as described beforehand. The cervical canal is provided with a series of inner cervical folds around which the leading end of the delivery tube must be manoeuvrerd as it is advanced along the canal. It is because the user is able to hold the uterus of the ewe steady with the locating tube that he is able to lift the flaps of the entry to the cervical canal and manoeuvre the delivery member around the inner cervical folds as it is advanced along the cervical canal. The delivery member ultimately arrives at the uterine cavity. The user then causes a charge of semen to be discharged from the delivery member and deposited in the uterine cavity. The semen may be in its natural state, or in a diluted state. The delivery member is then withdrawn, and the vacuum removed from the suction chamber 23. The locating tube may then be detached from the uterus of the ewe and withdrawn from her vagina.

When the apparatus is being used to inseminate maiden ewes, said other end of the delivery tube (i.e. that end which is provided with the offset) preferably tapers down to a rounded point. However, when artificially inseminating ewes which are not maidens, it is not necessary to use a tube with a tapered end. It would, of course, be necessary to provide the delivery tube with a rounded end so as not to inflict injury to the ewe during the artificial insemination operation.

It should be appreciated that the scope of the invention is not limited to the scope of the embodiment described. If, for example, future developments in the field of artificial insemination enable semen in a form other than its natural state or a diluted fluid state, to be deposited in the uterus to achieve conception, the delivery member may not necessarily be of tubular construction, but instead may be constructed so as to be capable of depositing the semen (in any such new form) into the uterus.

I claim:

1. Apparatus for artificial insemination of humans and other animals of the type having a reproductive system which includes a vagina and uterus, said apparatus comprising: a locating tube adapted for insertion into the vagina whereby one end thereof locates against the cervix of the uterus around the cervical canal; and a delivery member adapted to be passed along the locating tube and into the uterus for delivery of semen into the uterus; said delivery member being provided with a protrusion which is adapted to bear on the inner side wall of said locating tube to provide a fulcrum about which the delivery member may be pivoted.

2. Apparatus as claimed in claim 1 wherein means are provided for releasably securing said one end of the locating tube to the cervix.

3. Apparatus as claimed in claim 2 wherein the locating tube is adapted to be releasably secured at said one end to the uterus under the action of a suction force applied between the locating tube and the cervix of the uterus.

4. Apparatus as claimed in claim 3 wherein a suction chamber is located adjacent said one end of the locating tube and is open only at the end thereof corresponding to said one end of the locating tube, said open end of the suction chamber is adapted to be sealingly closed by the cervix when said one end of the locating tube is located against the cervix, whereby said suction force is applied between the locating tube and the cervix of the uterus when a vacuum or partial vacuum is created in the suction chamber.

5. Apparatus as claimed in claim 4 wherein a skirt surrounds that portion of the locating tube adjacent said one end thereof, the skirt in combination with that portion of the locating tube which the skirt surrounds defines said suction chamber.

6. Apparatus as claimed in claim 4 or 5 wherein an air line communicates at one end with the suction chamber and is adapted for connection at its other end to a vacuum source.

7. Apparatus as claimed in claim 6 wherein the skirt is rigid and is substantially flush at its outer end with said one end of the locating tube.

8. Apparatus as claimed in claim 7 wherein a light source is mounted on the locating tube.

9. Apparatus as claimed in claim 8 wherein the end portion of the locating tube remote from said one end of the locating tube is of enlarged cross-section with respect to the end portion adjacent said one end.

10. Apparatus as claimed in claim 9 wherein that end of the delivery member which is adapted to enter the uterus is formed with an off-set portion inclined to the central longitudinal axis of the delivery member.

11. Apparatus as claimed in claim 10 wherein said off-set portion is inclined at an angle of between 2° and 5° to said central longitudinal axis.

12. Apparatus as claimed in claim 1 wherein the protrusion is located towards that end of the delivery tube which is adapted to enter the uterus and is adapted to bear on the inner side wall of said end portion of the locating tube adjacent said one end of the locating tube.

13. Apparatus as claimed in claim 12 wherein the protrusion comprises a boss formed from transparent material.

14. Apparatus as claimed in claim 13 wherein the delivery member comprises a delivery tube one end of which is adapted to enter the uterus and the other end of which is adapted for connection to a supply of semen.

15. Apparatus as claimed in claim 14 wherein the delivery tube comprises an inner tube through which in use the semen is passed, and an outer tube which provides the inner tube with lateral stability.

16. Apparatus as claimed in claim 15 wherein the delivery member comprises a delivery section, a storage section and a plunger section, the delivery section being tubular and being adapted to enter the uterus the storage section being adapted to receive a tube containing supply of semen, said tube having a movable plug located at one end thereof, the plunger section being adapted to cause the plug to be advanced towards the other end of the tube and thereby cause semen to be discharged therefrom, the delivery section being in communication at one end with the storage section whereby said semen discharged from the tube enters said one end of the delivery section and discharges from the other end thereof.

17. Apparatus as claimed in claim 16 wherein said plunger section comprises a plunger which is adapted to bear on said plug and which is adapted to be actuated by the user.

* * * * *